ID#

(12) United States Patent
St. James

(10) Patent No.: US 7,306,816 B1
(45) Date of Patent: Dec. 11, 2007

(54) MEDICINAL PLANT COMPOSITIONS OF MATTER AND METHOD OF PREPARATION

(76) Inventor: Melanie Shane St. James, 1801 Lincoln Blvd., #138, Venice, CA (US) 90291

( * ) Notice: Subject to any disclaimer, the term of this patent is extended or adjusted under 35 U.S.C. 154(b) by 0 days.

(21) Appl. No.: 11/090,508

(22) Filed: Mar. 25, 2005

Related U.S. Application Data

(60) Provisional application No. 60/556,689, filed on Mar. 29, 2004.

(51) Int. Cl.
*A61K 36/00* (2006.01)
(52) U.S. Cl. .................................................. 424/725
(58) Field of Classification Search ................. None
See application file for complete search history.

*Primary Examiner*—Christopher Tate
*Assistant Examiner*—Catheryne Chen
(74) *Attorney, Agent, or Firm*—John Joseph Hall

(57) ABSTRACT

Compositions of matter comprising purified aqueous extracts of medicinal plants which are prepared by a method employing the steps of, rinsing the plant with clean water, boiling the plant in a boiler, allowing steam to escape carrying toxins from the plant, and filtering the resulting aqueous extract to produce a clear, clarified solution of the extract which has significant anti-HIV activity.

4 Claims, No Drawings

MEDICINAL PLANT COMPOSITIONS OF MATTER AND METHOD OF PREPARATION

Applicant claims priority of this application based upon Provisional Application No. 60/556,689, filed on Mar. 29, 2004, by applicant Melanie Shane St. James, under title METHOD OF PREPARING MEDICINAL REMEDY FROM AFRICAN PLANTS & PRODUCTS.

FIELD OF THE INVENTION

This invention relates generally to compositions of matter having therapeutically active properties derived from various medicinal plants and method of their preparation resulting in solutions containing extracts from such plants which are therapeutically active.

BACKGROUND OF THE INVENTION

It is commonly known that globally, about two-thirds of modern pharmaceutical products are based on ingredients derived from plants. For thousands of years, indigenous peoples have used plant based ingredients to treat various illnesses.

Generally, pharmaceutical companies use production methods to isolate a chemical compound which is reproduced and used as the active ingredient in new drugs.

However, these production methods do not provide for the use of many other active compounds and may not even identify them through chemical analysis. In some cases, the chemical compound so isolated may turn out to have less effective therapeutic properties while a more effective chemical compound remains unused in the production process.

On the other hand, herbal medicines are generally prepared by only a few rudimentary methods resulting in the use of alcohol as an extractive to produce alcohol based tinctures, or water as an extractive to produce teas, or concentrating the juice of a plant to form a syrup. These methods reflect a single step purification or an incomplete boiling process.

Herbal medicines produced by these methods do not have particulate matter, tannins, and toxins removed from the therapeutic extract, the presence of which diminishes the effectiveness of the extract by reducing absorption of the extract by the body.

SUMMARY OF THE INVENTION

It is, therefore, an object of the invention to provide a method for purification of specified medicinal plants by using several episodes of boiling of selected specified plant in water and allowing the resulting steam to escape at a specified time, the escaping steam taking with it toxins from the plant between episodes of boiling and filtering the resulting mixture to produce a clear solution of plant extract.

Another object of the invention is to provide a method for purification of specified medicinal plants which is relatively uncomplicated to perform.

A further object of this invention is to provide a method for purification of specified medicinal plants which does not require special equipment to be used in performing the steps of the method.

A yet further object of the invention is to provide aqueous compositions of matter comprising extracts derived from medicinal plants using the method of the invention and which has therapeutic inhibiting activity against the human immunodeficiency virus (HIV).

DETAILED DESCRIPTION OF THE INVENTION

Aqueous extracts forming the compositions of matter of the invention are derived from specified medicinal plants and are produced by the following method:

1. A quantity of the specified medicinal plant, including its leaves, branches, and roots is first rinsed with clean water for a suitable time, preferably at least two minutes.

2. A quantity of the specified medicinal plant is then placed in a tank boiler or other suitable pressurized steamer and covered with a sufficient amount of fresh water. A preferred quantity of the specified medicinal plant is about 10 kilograms and a preferred amount of fresh water is about 20 liters.

3. When steaming of the resulting mixture begins, about 20 liters more of fresh water is added and steaming is continued. A preferred steaming time is about 72 hours.

4. Preferably, the tank boiler is provided with a condensation system to safely release steam at intervals and allow the steam to condense and exit the tank boiler carrying with it soluble toxins of the specified medicinal plant. Preferably, the steam is released every 2 hours.

In the absence of a condensation system, the boiler may be opened after 36 hours of steaming to release steam which carries with it soluble toxins from the specified medicinal plant. Thereafter, steaming is continued for another 36 hours at a minimum.

5. Preferably, the tank boiler is provided with a stirring or agitating device so that the specified medicinal plant material may be stirred for more even heating and prevention of possible overheating. Such stirring and agitation need not be continuous but at suitable intervals of time such as every 5 to 10 minutes.

6. The total boiling time is preferably at least 72 hours but may be longer and does not need to be continuous as long as the overall boiling time is 72 hours.

7. After boiling is completed, the resulting boiled mixture is filtered, first through a thick pad of preferably cotton wool 2 to 4 inches thick. Other suitable filter material may be used to remove particulate matter in the boiled mixture. Next, to provide further clarification of the boiled mixture, the mixture is filtered through relatively fine filter paper, preferably of qualitative grade fine enough to produce a clear filtrate.

8. The resulting filtrate of aqueous extract of a specified medicinal plant is poured into storage containers, preferably 400 ml bottles, and sealed, preferably with aluminum foil or other suitable sealing material, and ready for use.

If further purification is desired, the bottles of aqueous extract are placed standing up in the tank boiler with their tops above water and boiled for an additional 36 hours. The resulting solution is then filtered again through filter paper of a qualitative grade and poured into sterilized glass bottles and sealed with a suitable sealing material.

Medicinal plants with therapeutic activity and which may be used in the above method to produce aqueous extracts may be selected from the following species:

1. *Datura stramonium,* 1st cultivar, has green leaves and purple branches;
2. *Datura stramonium,* 2nd cultivar, has white flowers and green branches;
3. *Vernonia karaguensis*
4. *Helichrysum cooperi*
5. *Indigofera rhynchocarpa*

6. *Cissampelos mucronata*
7. *Momordica boivinii*

The above medicinal plants have been found in Africa but may also be found in other lands.

The following examples illustrate the therapeutic activity of compositions of matter made from aqueous extracts produced by the above method in which plants from the above list were used.

EXAMPLE 1

An in vitro experiment was performed to test the anti-HIV activity of a composition of matter of the invention having the following composition by volume of aqueous extracts of specified medicinal plants prepared by the above described method of the invention:
1. 7% *Datura Stramonium*, 1st cultivar
2. 7% *Datura Stramonium*, 2nd cultivar
3. 45% *Vernonia karaguensis*
4. 4% *Helichrysum cooperi*
5. 15% *Indigofera rhynchocarpa*
6. 15% *Cissampelos mucronata*
7. 7% *Momordica boivinii*

A quantity of HIV infected blood cells was divided into two groups. One group was treated with the above composition of matter. The other group was not treated in any way.

After two weeks, the untreated group of HIV infected blood cells were transformed by growing into clusters, whereas the treated group of HIV infected blood cells remained essentially unchanged in appearance and resembled healthy uninfected blood cells and were not transformed into clusters.

The result was that the treatment of HIV infected blood cells with the above composition of matter inhibited replication of infected HIV blood cells.

Additional research regarding the therapeutic activity of medicinal plants has discovered that combining aqueous extracts of just two medicinal plants produces a composition of matter that has significant anti-HIV activity. These two medicinal plants are *Vernonia karaguensis* and *Momordica boivinii*.

EXAMPLE 2

A composition of matter was produced by mixing the following amounts by volume of aqueous extracts of *Vernonia karaguensis* and *Momordica boivinii* resulting from the above described method of the invention.
1. 50% *Vernonia karaguensis*
2. 50% *Momordica boivinii*

The above composition of matter was administered to an adult HIV/AIDS patient as follows:
Day 1—50 ml orally
Day 6—8 ml by intramuscular injection
Day 7—8 ml by suppository
Day 8—50 ml orally
Day 10—25 ml orally
Day 13—4 ml injection, 20 ml orally
Day 14—4 ml injection Before treatment, this patient had a CD4 cell count of 410. CD4 cells are a type of white blood cell known as lymphocytes or helper T cells and regulate the immune system and protect against infections. A normal range of CD4 cells in adults is from 600 to 1200 CD4 cells. The HIV virus infects CD4 cells and renders them useless.

After treatment, this patient had a CD4 cell count of 846, a normal count, indicating that the HIV virus had a substantially decreased presence in this patient. Also, the CD8 count increased from 447 to 912. Although the CD4/CD8 ratio did not appreciably change, 0.92 to 0.93, the increase in both types of cells is doubly significant because the CD8 cells are cytotoxic T cells which kill HIV infected CD4 cells and do not themselves get infected with HIV.

EXAMPLE 3

Another adult HIV/AIDS patient was treated with alternate dosages of a composition of matter comprising an aqueous extract of *Datura stramonium*, 1st cultivar and a composition of matter comprising an aqueous extract of *Momordica boivinii*, each extract being produced by the above described method of the invention.

Before treatment, this patient had a CD4/CD8 ratio of 141/396. After treatment, this patient had a CD4/CD8 ratio of 212/442, a small but significant improvement. The treatment regimen was as follows:

| Day | Composition of Matter | Dosage |
| --- | --- | --- |
| 1 | *Datura stramonium*, 1st cultivar (Ds) | 25 ml oral |
| 5 | Ds | 4 ml injection |
| 7 | *Momordica boivinii* (Mb) | 10 ml oral |
|  | Ds | 20 ml oral |
| 8 | Ds | 30 ml oral |
| 10 | Mb | 10 ml oral |
| 12 | Ds | 4 ml injection |
| 15 | Mb | 30 ml oral |
| 22 | Ds | 50 ml oral |
|  |  | 4 ml injection |
| 24 | Mb | 40 ml oral |
| 26 | Mb | 50 ml oral |
| 29 | Mb | 4 ml injection |
|  | Ds | 25 ml oral |
| 31 | Mb | 4 ml injection |
|  | Ds | 10 ml suppository |
| 33 | Mb | 25 ml oral |
| 36 | Mb | 2 ml injection |
| 38 | Ds | 47 ml oral |
| 41 | Mb | 50 ml oral |
| 48 | Ds | 10 ml suppository |

Since this patient had such a poor initial CD4/CD8 ratio, the improvement produced by the treatment indicated substantial progress toward lowering the presence of the HIV virus.

Although I have described my invention in detail with respect to preferred embodiments of the invention, it is understood that numerous changes may be made in the details of the steps of the method of the invention and the compositions of matter of the invention without departing from the spirit and scope of the invention as hereinafter claimed.

I claim:

1. A composition of matter having the capability of inhibiting replication of the human immunodeficiency virus, comprising:
   50% by volume of a first therapeutically active water extract solution from the medicinal plant *Vernonia karaguensis*,
   50% by volume of a second therapeutically active water extract solution from the medicinal plant *Momordica boivinii*,
   each of said extracts separately obtained by a method comprising:
   a. rinsing a suitable amount of one of the two specified medicinal plants with clean water for a suitable period of time, b. placing a suitable amount of said specified medicinal plant after said rinsing in a suitable boiler apparatus,
c. adding a suitable amount of water to cover said suitable amount of said specified medicinal plant,
d. boiling said suitable amount of said specified plant in said suitable boiler apparatus for a suitable period of time,
e. opening said suitable boiler apparatus to release steam carrying any toxins from said specified medicinal plant,
f. adding a suitable amount of water to maintain sufficient water to cover said suitable amount of said specified medicinal plant,
g. boiling said suitable amount of said specified medicinal plant in said suitable boiler apparatus for an additional suitable period of time,
h. filtering the resulting therapeutically active extract to remove particulate matter,
to produce said therapeutically active water extract solution from said specified medicinal plant.

2. A composition of matter having the capability of inhibiting replication of the human immunodeficiency virus, comprising:
7% by volume of a first therapeutically active water extract solution from the medicinal plant *Datura stramonium* (1st cultivar which has green leaves and purple branches),
7% by volume of a second therapeutically active water extract solution from the medicinal plant *Datura stramonium* (2nd cultivar which has white flowers and green branches),
45% by volume of a third therapeutically active water extract solution from medicinal plant *Vernonia karaguensis*,
15% by volume of a fourth therapeutically active water extract solution from the medicinal plant *Helichrysum cooperi*,
15% by volume of a fifth therapeutically active water extract solution from the medicinal plant *Indigofera Rhynchocarpa*,
15% by volume of a sixth therapeutically active water extract solution from the medicinal plant *Cissampelos mucronata*,
7% by volume of a seventh therapeutically active water extract solution from the medicinal plant *Momordica boivinii*,
each of said extracts separately obtained by a method comprising:
a. rinsing a suitable amount of a specified medicinal plant with clean water for a suitable period of time,
b. placing a suitable amount of said specified medicinal plant after said rinsing in a suitable boiler apparatus,
c. adding a suitable amount of water to cover said suitable amount of said specified medicinal plant,
d. boiling said suitable amount of said specified plant in said suitable boiler apparatus for a suitable period of time,
e. opening said suitable boiler apparatus to release steam carrying any toxins from said specified medicinal plant,
f. adding a suitable amount of water to maintain sufficient water to cover said suitable amount of said specified medicinal plant,
g. boiling said suitable amount of said specified medicinal plant in said suitable boiler apparatus for an additional suitable period of time,
h. filtering the resulting therapeutically active extract to remove particulate matter,
to produce said therapeutically active water extract solution from said specified medicinal plant.

3. A Composition of matter having the capability of contributing to a substantial increase of the CD4/CD8 ratio of a human HIV/AIDS patient, comprising:
a first therapeutically active water extract solution from the medicinal plant *Datura stramonium*, 1st cultivar, having green leaves and purple branches, and
a second therapeutically active water extract solution from the medicinal plant *Momordica boivinii*,
each of said extracts being administered separately at suitable intervals with suitable predetermined, oral, injected, and suppository dosages on a selective basis over a suitable period of time,
each of said extracts separately obtained by a method comprising:
a. rinsing a suitable amount of one of the two specified medicinal plants with clean water for a suitable period of time,
b. placing a suitable amount of said specified medicinal plant after said rinsing in a suitable boiler apparatus,
c. adding a suitable amount of water to cover said suitable amount of said specified medicinal plant
d. boiling said suitable amount of said specified plant in said suitable boiler apparatus for a suitable period of time,
e. opening said suitable boiler apparatus to release steam carrying any toxins from said specified medicinal plant,
f. adding a suitable amount of water to maintain sufficient water to cover said suitable amount of said specified medicinal plant,
g. boiling said suitable amount of said specified medicinal plant in said suitable boiler apparatus for an additional suitable period of time,
h. filtering the resulting therapeutically active extract to remove particulate matter,
to produce said therapeutically active water extract solution from said specified medicinal plant.

4. A method of administering alternately a therapeutically active aqueous extract of medicinal plant *Datura stramonium*, 1st cultivar and a therapeutically active aqueous extract of medicinal plant *Momordica boivinii* by administering separately suitable dosages orally, by injection, and by suppository, of each of said extracts alternately to an HIV infected patient to the HIV infected increase HIV patient's CD4/CD8 ratio over a suitable period of time, said extracts each obtained separately by a method comprising:
a. rinsing a suitable amount of a specified medicinal plant with clean water for a suitable period of time,
b. placing a suitable amount of said specified medicinal plant after said rinsing in a suitable boiler apparatus,
c. adding a suitable amount of water to cover said suitable amount of said specified medicinal plant
d. boiling said suitable amount of said specified plant in said suitable boiler apparatus for a suitable period of time,
e. opening said suitable boiler apparatus to release steam carrying any toxins from said specified medicinal plant,
f. adding a suitable amount of water to maintain sufficient water to cover said suitable amount of said specified medicinal plant,
g. boiling said suitable amount of said specified medicinal plant in said suitable boiler apparatus for an additional suitable period of time,
h. filtering the resulting therapeutically active extract to remove particulate matter,
to produce said therapeutically active water extract solution from said specified medicinal plant.

* * * * *